(12) United States Patent
Uber et al.

(10) Patent No.: US 7,835,004 B2
(45) Date of Patent: Nov. 16, 2010

(54) GAS SENSORS AND METHODS OF CONTROLLING LIGHT SOURCES THEREFOR

(75) Inventors: Robert E. Uber, Pittsburgh, PA (US); John H. Reno, II, Valencia, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 121 days.

(21) Appl. No.: 11/899,508

(22) Filed: Sep. 6, 2007

(65) Prior Publication Data

US 2009/0009769 A1    Jan. 8, 2009

Related U.S. Application Data

(60) Provisional application No. 60/958,328, filed on Jul. 3, 2007.

(51) Int. Cl.
*G01N 21/00* (2006.01)
(52) U.S. Cl. .................................................. 356/437
(58) Field of Classification Search ......... 356/335–343, 356/432–440, 213–218
See application file for complete search history.

(56) References Cited

U.S. PATENT DOCUMENTS

| | | | | |
|---|---|---|---|---|
| 3,327,139 A | * | 6/1967 | Hillman | 327/331 |
| 4,632,549 A | * | 12/1986 | Czabaffy et al. | 356/300 |
| 4,755,648 A | * | 7/1988 | Sawa | 219/661 |
| 4,902,958 A | | 2/1990 | Cook, II | 323/282 |
| 5,387,979 A | * | 2/1995 | Brauer et al. | 356/435 |
| 2004/0145741 A1 | * | 7/2004 | Cole et al. | 356/436 |
| 2008/0024656 A1 | * | 1/2008 | Huang | 348/372 |

FOREIGN PATENT DOCUMENTS

EP          0584519       3/1994
WO          WO 9853646    11/1998

OTHER PUBLICATIONS

V. Jayaram Menon and Dulli C. Agrawal, Banaras Hindu University, Varanasi, India, "Switching Time of a 100 Watt Bulb," Physical Education, vol. 34, No. 1, Jan. 1, 1999.

* cited by examiner

*Primary Examiner*—Hoa Q Pham
(74) *Attorney, Agent, or Firm*—Henry E. Bartony, Jr.; James G. Uber

(57) ABSTRACT

A gas sensor includes a light source, a power source in operative connection with the light source and a control system in operative connection with the light source and the power supply. The control system is adapted to control power input from the power source to the light source such that the time period of the control frequency is shorter than the thermal time constant of at least one of (i) the infrared light source, (ii) the gas within the sensor, or (iii) a detector of the sensor. The time period of the control frequency can, for example, be no greater than ⅓ of the thermal time constant, no greater than 1/10 of the thermal time constant, or even no greater than 1/20 of the thermal time constant. A feedback signal can be provided to the control system assist in achieving control.

20 Claims, 4 Drawing Sheets

GAS SENSORS AND METHODS OF CONTROLLING LIGHT SOURCES THEREFOR

RELATED APPLICATIONS

This application claims priority on U.S. Provisional Patent Application No. 60/958,328 filed Jul. 3, 2007, the entire disclosure of which is incorporated herein by reference

BACKGROUND OF THE INVENTION

The present invention relates generally to gas sensors, and, more particularly, to gas sensors including a light source and method of controlling light sources therefor.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

A number of gas sensors use energy from various types of light sources in the detection methodology of the gas sensor. For example, the use of gas sensors to detect the concentration level of gaseous species of interest using the photoacoustic effect is well known. For example, U.S. Pat. No. 4,740,086, the disclosure of which is incorporated herein by reference, discloses the use of a photoacoustic gas sensor to convert the optical energy of an amplitude modulated light source into acoustic energy when the light mechanically and thermally excites the gaseous species of interest as it diffuses into a sensing chamber upon which the light is incident. Sound waves of an intensity corresponding to the concentration level of the gas within the chamber are generated as the light radiation absorbed by the gas creates pressure fluctuations of a magnitude proportional to the number of gas molecules located within the sensing chamber. These sound/pressure waves are detected by a pressure sensor or acoustic detector such as a microphone.

Photoacoustic gas sensors can also have mechanical valves to let in the sample gas when open, which then close to trap the sample gas, block external acoustical noise and allow photoacoustic pressure to build up. Valves have the disadvantages of requiring energy to operate and of having moving parts which wear out leading to limited lifetimes (typical 0.5 to 3 years). Alternatively, gas diffusion element(s) such as described in U.S. Pat. No. 4,740,086, can be used to simultaneously allow gas diffusion, allow photoacoustic pressure to build up and attenuate external acoustical noise.

Whether a photoacoustic sensor includes a valve system or one or more gas diffusion elements, the operation and control of infrared light sources used therein continues to pose problems. In that regard, infrared light sources from different manufacturers can have different internal resistances. Care must be taken to avoid overheating or damaging various light sources with excessive electrical energy. However, under known control methodologies, overheating may occur, resulting in a decrease in the operational life of the light source.

Further, an infrared light source may have a lower electrical resistance when cold (such as at power up) than when at normal operating temperature. The electrical resistance of the light source when cold may even be too low to allow the power supply circuit of the photoacoustic gas sensor to start the light source. Today, manufacturers must build power supplies for photoacoustic gas sensors overly robust to start the power supply circuit under all temperature conditions, thereby requiring larger and/or higher rated components at additional cost. Also, a typical installation may have multiple photoacoustic gas sensors wired to a single power supply transformer that today must be overly robust to be able to start all the sensors at power up.

Similar problems can occur in other types of gas sensors in which energy from a light source interacts with an analyte to create an output signal. For example, such problems can occur in gas sensors in which the measuring method is based on the principle of light absorption in the infrared region known as non-dispersive infrared absorption (NDIR). In such sensors, broadband infrared radiation produced by the light source passes through a chamber filled with gas (for example, methane or carbon dioxide). The gas absorbs radiation of a known wavelength and this absorption is a measure of the concentration of the gas. There is typically a narrow bandwidth optical filter at one or both ends of the chamber to remove all other wavelengths of light before it is measured with an infrared detector or detectors, such as a pyroelectric detector or a thermopile detector.

In the case of a Light Emitting Diode (LED) or laser diode light source, it may be desirable to modulate the light source at higher frequencies than is desired for a photoacoustic sensor or an NDIR sensor. LEDs and laser diodes are typically non-linear semiconductor devices since the light output does not always increase in proportion to the increase in the input electrical power. For example, at the low end of the operating range, if the input power is doubled, the light output may more than double. At the upper end of the operating range, the lifetime of the LED or laser diode may be reduced by thermal effects of the electrical current flowing in the semiconductor junction. Generally, this leads to each device having an input power operating point with optimum efficiency and lifetime. Similarly, LEDs and laser diodes are often built to operate at frequencies ranging from D.C. to hundreds of megahertz (MHz). Operating a non-linear device at a modulated frequency allows the higher non-linear optical outputs while the electrical current is flowing and allows the device to cool when the electrical current is not flowing, for a reduced average power level for a longer lifetime. Thus the individual details of each device construction will also tailor an optimum modulation frequency, input power and lifetime for the device. This optimum modulation frequency may be higher than the desired frequency for a photoacoustic sensor or for an NDIR sensor.

It thus remains desirable to develop improved gas sensors, devices for use in gas sensors and methods of control of light sources used in gas sensors.

SUMMARY OF THE INVENTION

In one aspect, the present invention provides a gas sensor including a light source, a power source in operative connection with the light source and a control system in operative connection with the light source and the power supply. The control system is adapted to control power input from the power source to the light source such that the time period of the control frequency is shorter than the thermal time constant of at least one of (i) the infrared light source, (ii) the gas within the sensor, or (iii) a detector of the sensor. The time period of the control frequency can, for example, be no greater than $\frac{1}{3}$ of the thermal time constant, no greater than $\frac{1}{10}$ of the thermal time constant, or even no greater than $\frac{1}{20}$ of the thermal time constant. A feedback signal can be provided to the control system to assist in achieving control.

In another aspect, the present invention provides a photoacoustic gas sensor including a measurement chamber, an infrared light source in optical connection with the measurement chamber, a power source in operative connection with the light source and a control system in operative connection with the light source and the power supply. The control system is adapted to control power input from the power source to the light source such that the time period of the control frequency is shorter than the thermal time constant of at least one of (i) the infrared light source, (ii) the gas within the sensor or (iii) a detector of the sensor.

In a further aspect, the present invention provides a method of operating a light source for a gas sensor including controlling power input to the light source such that the time period of the control frequency is shorter than the thermal time constant of at least one of (i) the light source, (ii) the gas within the sensor or (iii) a detector of the sensor. As described above, the time period of the control frequency is no greater than $1/3$ of the thermal time constant, no greater than $1/10$ of the thermal time constant, or even no greater than $1/20$ of the thermal time constant.

The light source can, for example, be an infrared light source. The light source can, for example, be an etched silicon infrared light source.

Power input to the light source can, for example, be controlled to obtain a sine wave modulation of the output of the light source (for example, an infrared light source). Power input to the light source can also, for example, be controlled to obtain a sine wave modulation of a sensor output signal.

A feedback signal can be provided to assist in achieving control. The feedback signal can, for example, be provided from an optical sensor. The optical sensor can be a photodiode.

An average voltage supplied to the light source can, for example, be increased over multiple operational periods after start up of the light source.

In several embodiments, pulse width modulation is used to control power supplied to the light source. The frequency of pulses can also be modulated to control power supplied to the light source.

The light source can, for example, emit energy in both the visible and infrared range and the feedback signal can, for example, be provided in the visible range.

The present invention, along with the attributes and attendant advantages thereof, will best be appreciated and understood in view of the following detailed description taken in conjunction with the accompanying drawings.

DETAILED DESCRIPTION OF THE INVENTION

Several representative embodiments of the present invention are described herein in connection with photoacoustic gas sensors. One skilled in the art appreciates, however, that the devices, systems and methods of the present invention can be used in connection with virtually any type of gas sensor in which an analyte interacts with energy from a light source.

Figure 1:
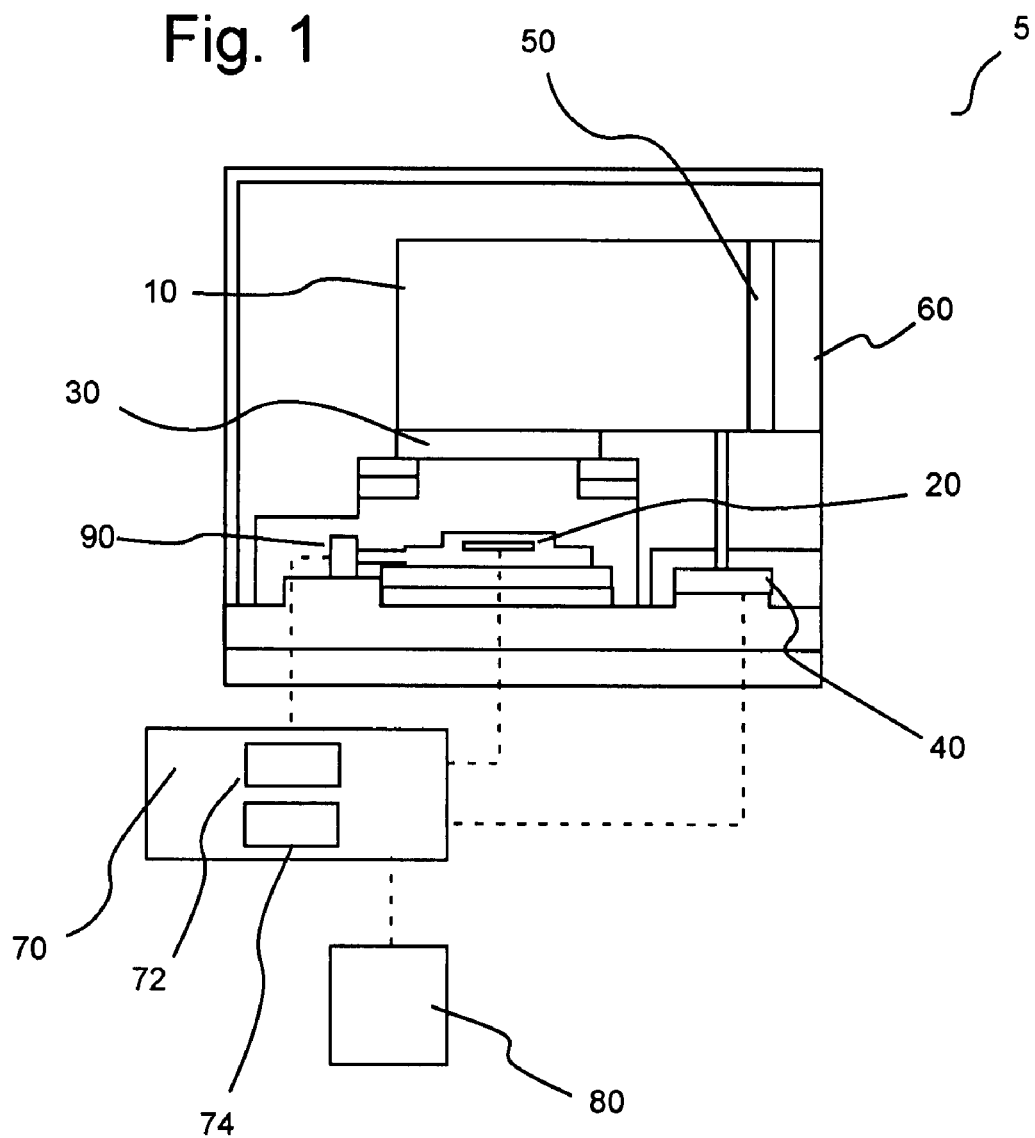
FIG. 1 illustrates an embodiment of a photoacoustic gas sensor of the present invention.

FIG. 1 illustrates a representative embodiment of a photoacoustic sensor 5 of the present invention which includes a sensing chamber or measurement chamber 10. An infrared light source 20 is in optical connection with measurement chamber 10 via a window 30. An acoustic pressure sensor 40 (for example, a pressure transducer or a microphone) is in operative connection with measurement chamber 10. One or more gas diffusion elements 50 can, for example, be placed between gas inlet 60 and the measurement chamber 10 to attenuate pressure waves while allowing diffusion of analyte gas molecules therethrough. Diffusion element 50 can, for example, be a sintered metal element as known in the art. As an alternative to one or more diffusion elements, a valve system, as known in the art, can be used.

Photoacoustic sensor 5 further includes a control system 70 that can, for example, include a computer processor 72 (for example, a microprocessor) and a memory system 74 in communicative connection with processor 72. Control software can, for example, be stored in memory system 74. A power source 80 is also in operative connection with control system 70 and with infrared light source 20. An optical sensor 90 (for example, a photodiode) is in operative connection with control system 70 to, for example, provide feedback from infrared light source 20.

Figure 2:
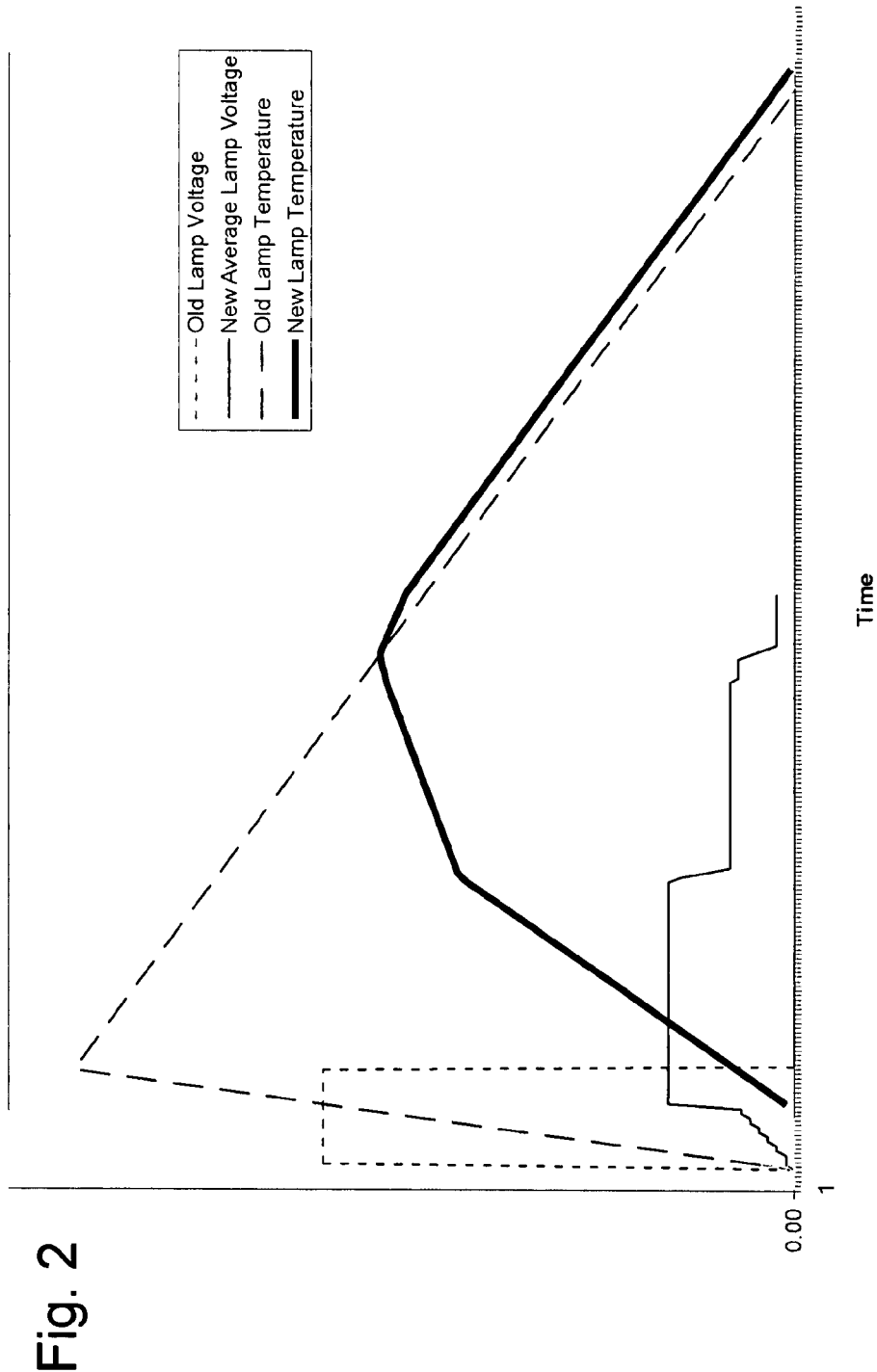
FIG. 2 illustrates a comparison of a control method of the present invention compared to a control method used in currently available photoacoustic gas sensors.

As described above, internal electrical resistances (both when cold at the time of power up and when at operating temperature) can vary between infrared light sources, and overheating of an infrared light source can pose problems and significantly shorten the operative life of the infrared light source. The increased use of relatively small light sources (for example, etched silicon infrared light sources) of relatively low thermal mass in gas sensors exacerbates such problems of overheating. LEDs, laser diodes, and other light sources are also susceptible to damage from too much electrical power, requiring careful control. FIG. 2 illustrates a comparison of a power input control scheme used in currently available photoacoustic gas sensors for the control of the output of the infrared light source thereof (dashed lines) with a control scheme of the present invention (solid lines). Under current practice, relatively long (in time duration) pulses of energy from a power source are supplied to a light source with a single pulse applied at the beginning of each operational period. The present inventors have discovered that operating an infrared light source by controlling power input to the light source such that the time period of the control frequency is shorter than the thermal time constant of the infrared light source results in good control of and improved operational lifetime for the light source. Alternately, controlling power input to the light source such that the time period of the control frequency is shorter than the thermal time constant of the gas inside the photoacoustic sensor will similarly result in good control of and improved operational lifetime for the light source. And alternately, controlling power input to the light source such that the time period of the control frequency is shorter than the thermal time constant of the detector in an NDIR sensor will similarly result in good control of and improved operational lifetime for the light source.

A typical or representative operational frequency for photoacoustic light source 20 used in several embodiments of the photoacoustic gas sensors of the present invention is approximately 18 Hz (Hertz). A typical thermal time constant of, for example, an etched silicon infrared light source is, for example, approximately 20 ms (milliseconds). The thermal time constant can be defined generally as the amount of time required for an element or entity such as the light source, or the gas within a sensor or the thermal mass of the detector (for example, in an NDIR sensor) to change its body temperature by 63.2% of a specific temperature step change when the measurements are made under zero-power conditions in thermally stable environments. As described above, power input to light source 20 is controlled in the present invention such that the time period of the control frequency is shorter than the thermal time constant. Preferably, the time period of the control frequency is no greater than 1/3 of the thermal time constant. The time period of the control frequency can also, for example, be no greater 1/10 of the thermal time constant, or no greater than 1/20 of the thermal time constant, or even no greater than 1/40 of the thermal time constant. In several embodiments of the present invention, the input from power source 80 was modulated at a control frequency (f) of 4 kHz (kilohertz) or greater. A control frequency of 4 kHz or 4000 Hz results in a pulse time period or the control time period (T; 1/f) of 0.25 milliseconds or 250 microseconds.

An LED or laser diode light source may have optimum modulation frequencies higher than the desired frequency for a photoacoustic sensor or for an NDIR sensor. For example, an LED may perform best when modulated at 4 kHz or higher while the photoacoustic sensor 5 of the present embodiment operates at approximately 18 Hz. In this case the light output of the LED is modulated at 4 kHz and is not low-pass filtered by its thermal time constant because of the short lifetime constant of the electron-hole pairs in the semiconductor junction. Instead, in a photoacoustic sensor, the low-pass filtering is provided by the several millisecond (~2 to 10 msec) thermal time constant of the gas molecules as it absorbs a photon which raises an electron to a higher energy state and then through collisions with other molecules will relax this higher energy state to heat. Alternately, in an NDIR sensor, the low pass filtering can be provided by the thermal mass of the thermopile or the pyroelectric detectors with typical 1 to 10 millisecond time constants.

Figure 3:
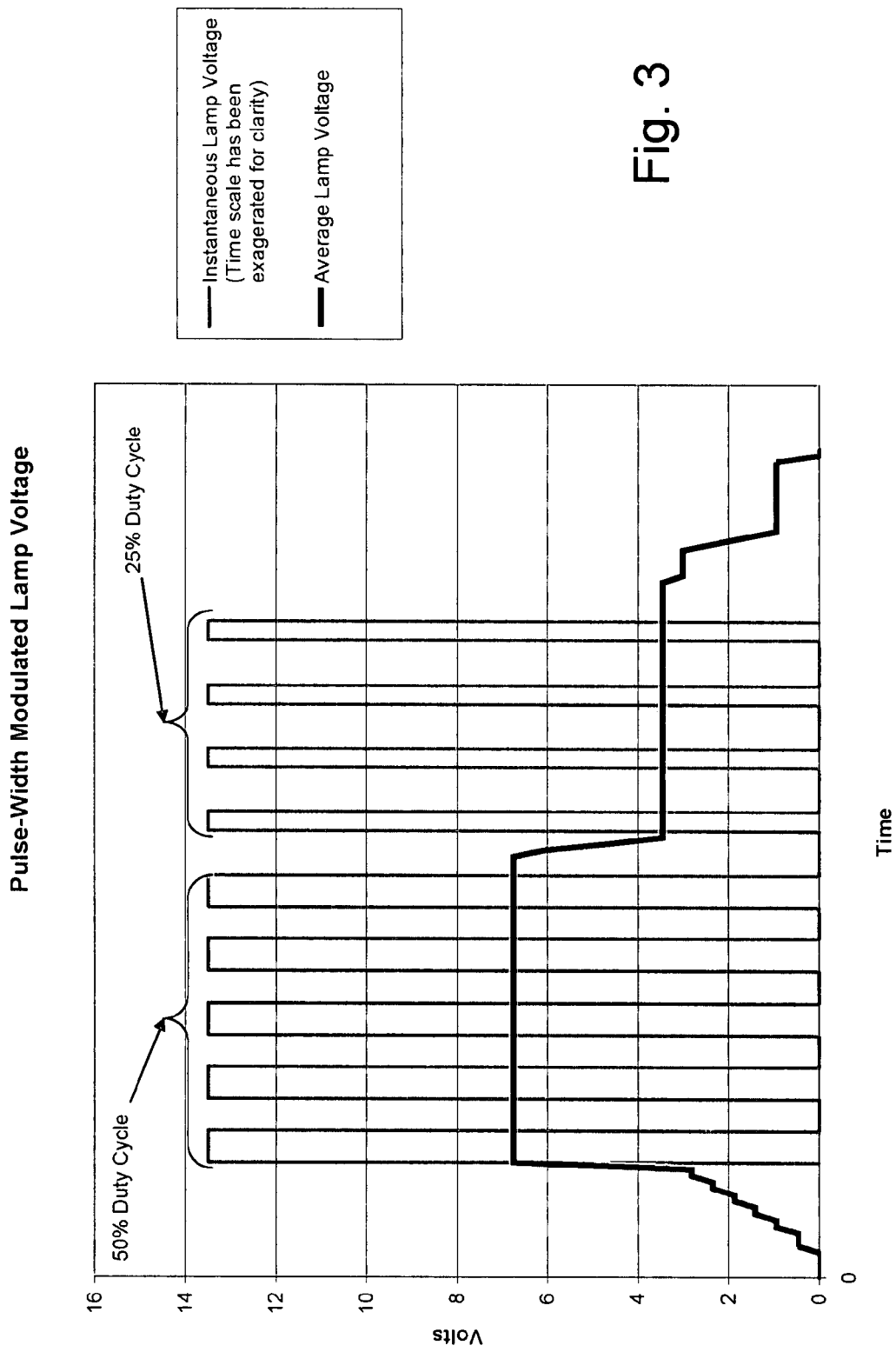
FIG. 3 illustrates further details of a control method of the present invention used to obtain a sine wave modulation of the infrared light source output or a sine wave modulation of the photoacoustic output signal.
Figure 4:
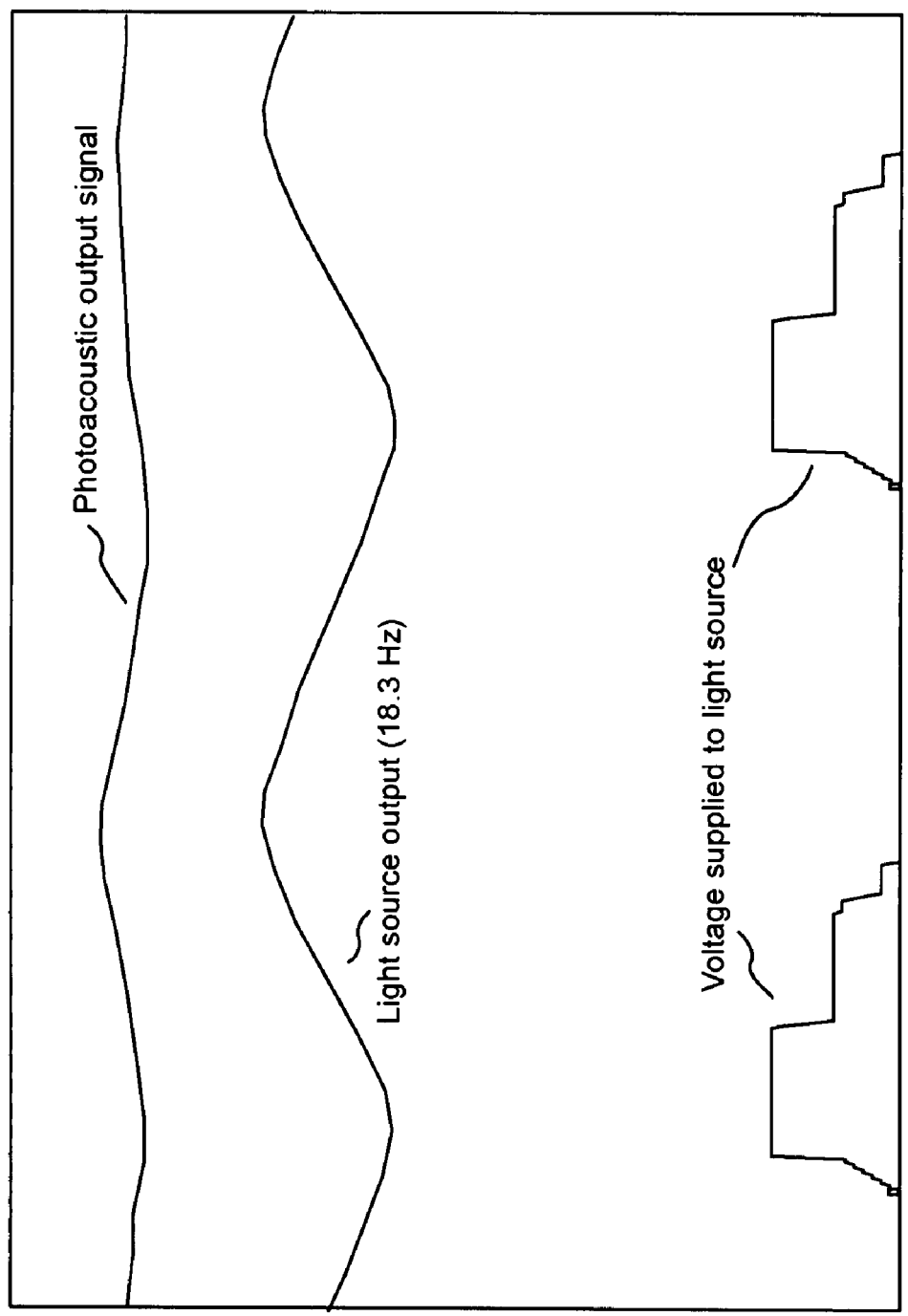
FIG. 4 illustrates an experimental example of the generation of a sine wave modulation of the infrared light source output and a sine wave modulation of the photoacoustic output signal using a control methodology of the present invention

In the embodiments illustrated in FIGS. 2 through 4, power input to light source 20 from power supply 80 is controlled to obtain a sine wave modulation of the output of light source 20 (middle curve in FIG. 4) or to obtain a sine wave modulation of a photoacoustic output signal (upper curve in FIG. 4). In the case that power supply 80 is controlled to obtain a sine wave modulation of the output light source 20, feedback can, for example, be provided to control system 70 from optical sensor 90 (for example, a photodiode) to facilitate control of the power input to light source 20. In several embodiments, light source 20 can emit energy over a range of wavelengths including wavelengths in the visible spectrum and in the infrared spectrum. While infrared light from such a light source 20 is used to interact with the analyte gas, light closer to the visible spectrum can be used in the feedback control loop. The ready availability of inexpensive optical sensors 90 for detection of light close to and in the visible spectrum can provide cost savings.

In the case that power supply 80 is controlled to obtain a sine wave modulation of the photoacoustic output signal, a feedback can, for example, be provided to control system 70 from pressure sensor 40 (for example, a microphone). In several embodiments, a reference volume of a known gas can be provided to ensure that a signal is present. Alternatively, the background solid-state photoacoustic effect may be sufficient to ensure that a signal is present. In the illustrated embodiment, the amplitude of the power input is modulated at a frequency (f) of 4 kHz (kilohertz), resulting in a time period (T; 1/f) of 0.25 ms or 250 microseconds.

For example, when the light source 20 is at a normal operating average temperature after many operational periods, the modulated amplitude of the power supplied to light source 20 can be larger at the beginning of a control cycle when light source 20 is comparatively cooler, and can be decreased later in the control cycle when light source 20 is comparatively warmer. In the control protocol illustrated, for example, in FIG. 4, the power delivered to light source 20 was partially reduced about halfway through the on period and then greatly reduced or stopped near a maximum of the light source output sine wave. Power modulation was then resumed near a minimum of the light source output sine wave. In addition or alternatively to pulse width modulation of the amplitude of the power supplied to light source 20, the control frequency of the pulses can be modulated with, for example, a fixed pulse width to accomplish similar IR source power modulation.

As described above, an infrared light source typically has a lower resistance when cold at power up than when at normal operating temperature. The relatively short time period of the control frequency in the present invention allows light source 20 to be warmed up gradually over several operational periods without drawing down the power supply. In the case of an operational frequency of 18 Hz, each operational period would be 1/18 Hz or approximately 0.0555 seconds (or 55.5 milliseconds). The gradual warm up may typically be accomplished over 500 operational periods or about 30 seconds. Optimization of the duty cycle and control frequency depends upon the thermal characteristics of a particular light source and is readily accomplished by those skilled in the art. The control systems and methodologies of the present invention enable manufacturers to incorporate power supplies within photoacoustic gas sensors that are smaller and less robust at handling peak current draws than those currently used in photoacoustic or NDIR sensors, thereby providing significant cost savings. Moreover, the control methodologies of the present invention can be used in connection with light sources of widely varying internal resistance when at operating temperature and when cold at power on.

In several embodiments, pulse width modulation was used to control the average energy delivered to the light source. Pulse width modulation is a well known control technique used to control the average power and/or energy delivered to a load. A simple empirical example that helps to explain pulse-width modulation is the home thermostat. When the home is too cold, the thermostat activates the furnace which begins to warm the air. After several minutes, when the desired temperature is obtained, the thermostat turns the furnace off. The cycle is repeated as needed to maintain a desired temperature.

Instead of a furnace that burns fuel, in the embodiments of the present invention a voltage is supplied to, for example, a light source filament or other radiant element to heat the light source filament to a desired temperature of several hundred degrees Celsius. Because the light source systems of the present invention are so much smaller with lower thermal mass, the cycle times are much shorter than compared to the operation of a furnace. For example, a cycle time of approximately 55 milliseconds between one heating cycle and the next can be used.

Applying voltage to the light source 100% of the time achieves a maximum filament temperature, while applying voltage to the light source 0% of the time achieves a minimum temperature. The temperature can be set to any level between these two extremes by adjusting the duty cycle to an intermediate value. This number, between 0 and 100, is called the Pulse-Width-Modulation level, or PWM level.

In the embodiments described above the output of light source 20 was varied in a sinusoidal fashion. The optical output of light source 20 is related to temperature on the order of $T^4$, wherein T is temperature. Thus, a series of PWM levels was used to effect control as illustrated in FIG. 4. In several embodiments, the level was updated approximately every 250 microseconds. There were 256 different pulse width levels that may be selected in order during each cycle. Therefore, it takes approximately 64 milliseconds (250 microseconds× 256) to complete each complete cycle. Cycles were repeated indefinitely during operation of gas sensor 5. The result was a sine wave having a frequency of approximately 18 Hz or a period of approximately 55.5 milliseconds.

The sine wave timing is fixed by the crystal frequency of microprocessor 72. However, the magnitude of the signal can vary with, for example, ambient temperature, changes in power supply voltage, and aging of the light source. Thus, it is preferable to provide a mechanism of measuring the optical power or energy and controlling the system to adjust the output to maintain the energy at relatively a consistent level. That measurement was performed by optical transducer 90 (a photo-diode) and a software algorithm (as known in the control arts) executed by microprocessor 72 that extracted the energy level at approximately 18 Hz. The acquired information was used to adjust the values up or down in a PWM table in memory system 74 to maintain the target energy level. In several studies, the adjustment range of this multiplier was 0.01 to 2.00.

As described, above, light sources often fail at power up as a result of the sudden inrush of current applied to a cold material. In several embodiments of the present invention, the multiplier was set to 0.01 at power up, so the inrush current was minimized. This method has the added benefit that the power supply did not need to supply the large inrush current. As an example, the light source used in one study of a $CO_2$ Photoacoustic sensor of the present invention had a hot resistance of approximately 50 ohms, but a cold resistance of only 5 ohms. If 13.5 Volts were applied to light source, the current with a hot filament would be 270 milliamps. However, the current with a cold filament under the same applied voltage would be 10 times larger at 2.7 Amps. By reducing the energy by a multiple of 0.01, cold current was reduce to as little as 27 milliamps. The multiplier was gradually raised over a number of operational periods (for example, over the first minute after startup or over approximately the first 1080 operational periods so that the highest current the power supply was required to deliver was only the 270 mA current delivered to the hot filament. This control methodology allowed the power supply of the photoacoustic gas sensors of the present invention to be 10 times smaller in capacity than those used in currently available photoacoustic gas sensors. Because the loop or feedback control of the present invention accommodates changes in light source voltage, the regulation of the power supply is also less critical than is the case in currently available photoacoustic or NDIR sensors.

The advantages of the control methodology of the present invention are further illustrated upon comparison of another simple method for reducing the voltage and electrical power delivered to a load such as light source 20; that is, by inserting a resistance in series with the load. For example, in several embodiments of photoacoustic gas sensor systems of the present invention the power supply output was 13.5 Volts and the light source had a resistance of about 50 ohms as described above. To reduce the voltage at the lamp to 6.75 volts, one could place a 50 ohm resistor in series with the lamp. Unfortunately, the resistor would dissipate the same amount of power as the lamp; in this case 0.911 Watts (using the formula Power=Volts$^2$/Resistance).

Referring primarily to FIG. 3, in a pulse width modulation control methodology of the present invention, the series resistor described above is replaced with a solid-state switch such as a transistor. When the control circuitry causes the transistor to conduct, the full power source voltage is applied to the load. Conversely, when the control circuitry causes the transistor to impede conduction, no voltage is applied to the load. These pulses are applied in a controlled pattern as described above. The average voltage can be controlled by adjusting the ratio of the time that voltage is applied to the time that voltage is withheld. This is described using the formula: Average voltage=(power source voltage)*On-Time/(On-Time+Off-Time). In this embodiment, the period of the pulse (On-Time+ Off-Time) is, for example, 250 microseconds and the full power source voltage is 13.5 Volts. To set the average lamp voltage to 50% of the full lamp voltage (6.75 Volts), the on-time can be set to 50% of the pulse period, for example, 125 microseconds. If we choose to further reduce the average voltage to 25% (3.38 Volts) the on-time is reduced to 62.5 microseconds.

The formula Power=Volts$^2$/Resistance can also be applied to the transistor used in the pulse width modulation circuit. When the transistor conducts, its impedance is less than 0.5 ohms, which causes the voltage developed across the transistor to remain below 0.134 Volts, limiting the power dissipation of that component to 0.036 Watts. When the transistor does not conduct, its impedance is greater than 1,000,000 ohms and the voltage will be 13.5 Volts, resulting in a power dissipation of less than 0.0002 Watts. Therefore, when the transistor is driven with a 50% duty-cycle to apply an average voltage of 6.75 Volts to the lamp, 0.018 Watts is lost (0.036+ 0.0002)/2=0.018), which is approximately 1/50th the power lost by the resistor described above.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A gas sensor, comprising: a light source to irradiate gas within the gas sensor with light energy, a detector to measure a response, a power source in operative connection with the light source and a control system in operative connection with the light source and the power supply, the control system being adapted to control power input to the light source from the power source such that the time period of a control frequency of power input to the light source is shorter than the thermal time constant of at least one of the light source, the gas within the sensor, and the detector of the sensor.

2. The gas sensor of claim 1 wherein the time period of the control frequency is no greater than 1/3 of the thermal time constant.

3. The gas sensor of claim 1 wherein the time period of the control frequency is no greater than $1/10$ of the thermal time constant.

4. The gas sensor of claim 1 wherein the time period of the control frequency is no greater than $1/20$ of the thermal time constant.

5. The gas sensor of claim 1 wherein a feedback signal is provided to the control system assist in achieving control.

6. A photoacoustic gas sensor, comprising: a measurement chamber, an infrared light source in optical connection with the measurement chamber to irradiate gas within the measurement chamber with infrared light energy, a detector to measure a response, a power source in operative connection with the light source and a control system in operative connection with the light source and the power supply, the control system being adapted to control power input to the light source such that the time period of a control frequency of power input to the light source is shorter than the thermal time constant of at least one of the infrared light source, a gas within the sensor and the detector of the sensor.

7. A method of operating a light source for a gas sensor in which light energy from the light source irradiates a gas within the sensor and a detector measures a response, comprising: controlling power input to the light source such that the time period of a control frequency of power to the light source is shorter than the thermal time constant of at least one of the light source, the gas within the sensor and the detector of the sensor.

8. The method of claim 7 wherein the time period of the control frequency is no greater than $1/3$ of the thermal time constant.

9. The method of claim 7 wherein the time period of the control frequency is no greater than $1/10$ of the thermal time constant.

10. The method of claim 7 wherein the time period of the control frequency is no greater than $1/20$ of the thermal time constant.

11. The method of claim 7 wherein power input to the light source is controlled to obtain a sine wave modulation of the output of the light source or power input to the light source is controlled to obtain a sine wave modulation of a sensor output signal.

12. The method of claim 11 wherein a feedback signal is provided to assist in achieving control.

13. The method of claim 7 wherein the light source is controlled to obtain a sine wave modulation of the output of the light source.

14. The method of claim 13 wherein the feedback signal is provided from an optical sensor.

15. The method of claim 14 wherein the optical sensor is a photodiode.

16. The method of claim 13 wherein the light source emits energy in both the visible and infrared range and the feedback signal is provided in the visible range.

17. The method of claim 7 wherein an average voltage supplied to the light source is increased over multiple operational periods after start up of the light source via control of modulation of power to the light source.

18. The method of claim 7 wherein pulse width modulation is used to control power supplied to the light source.

19. The method of claim 7 wherein the light source is an infrared light source.

20. The method of claim 7 wherein frequency of pulses is modulated to control power supplied to the light source.

\* \* \* \* \*